United States Patent
Li et al.

(10) Patent No.: US 7,641,836 B2
(45) Date of Patent: *Jan. 5, 2010

(54) TISSUE REPAIR DEVICE AND FABRICATION THEREOF

(75) Inventors: Zhigang Li, Hillsborough, NJ (US); Kevin Cooper, Flemington, NJ (US); Yufu Li, Bridgewater, NJ (US); Raymond S. Shissias, Iselin, NJ (US); Qiang Zhang, Annandale, NJ (US)

(73) Assignee: Ethicon, Inc., Somerville, NJ (US)

( * ) Notice: Subject to any disclaimer, the term of this patent is extended or adjusted under 35 U.S.C. 154(b) by 816 days.

This patent is subject to a terminal disclaimer.

(21) Appl. No.: 11/159,698

(22) Filed: Jun. 23, 2005

(65) Prior Publication Data

US 2007/0001341 A1 Jan. 4, 2007

(51) Int. Cl.
*B29C 43/18* (2006.01)
*A61B 17/00* (2006.01)
(52) U.S. Cl. ............... 264/274; 606/300; 606/230
(58) Field of Classification Search ............ 264/279, 264/271.1, 274; 606/301, 310, 311, 312, 606/318, 154, 230
See application file for complete search history.

(56) References Cited

U.S. PATENT DOCUMENTS

| | | | | |
|---|---|---|---|---|
| 4,043,690 | A | * | 8/1977 | Browne .................. 403/268 |
| 5,152,945 | A | | 10/1992 | Thicthener et al. |
| 5,641,501 | A | * | 6/1997 | Cooper et al. ............. 424/426 |
| 5,674,286 | A | | 10/1997 | D'Alessio et al. |
| 5,964,783 | A | | 10/1999 | Grafton et al. |
| 6,083,522 | A | | 7/2000 | Chu et al. |
| 6,147,135 | A | * | 11/2000 | Yuan et al. ................ 523/105 |
| 6,641,597 | B2 | | 11/2003 | Burkhart et al. |
| 2002/0087190 | A1 | | 7/2002 | Benavitz et al. |
| 2003/0187444 | A1 | | 10/2003 | Overaker et al. |
| 2003/0187446 | A1 | | 10/2003 | Overaker et al. |

FOREIGN PATENT DOCUMENTS

EP 0664198 6/1999

* cited by examiner

*Primary Examiner*—Matthew J. Daniels
(74) *Attorney, Agent, or Firm*—Emil Richard Skula

(57) ABSTRACT

A device for use in tissue repair procedures, a surgical tissue repair procedure, and a method of making the device. Specifically, the device is an assembly of a cannulated anchor member with a cord passed through it, and a stopper mounted to an end of the cord to prevent the cord from passing back through the anchor member.

7 Claims, 3 Drawing Sheets

TISSUE REPAIR DEVICE AND FABRICATION THEREOF

FIELD OF THE INVENTION

The present invention relates to medical devices. More specifically medical devices for use in tissue repair, surgical procedures for repairing tissue using such devices, and a method of making the devices.

BACKGROUND OF THE INVENTION

There are many applications in the field of orthopaedics for medical devices used in hole. A solid and secure attachment between the cord and anchoring components of anchor devices is essential to the success of the device. Such conventional devices include vertebral straps, suture anchors, and suture staples.

Conventionally known methods for attaching or securing cords to anchoring components include insert molding, passing the cords through eyelets or small holes in the anchoring components, compressing the cord between surfaces of the device, etc. Although generally satisfactory for their intended purpose, there may be certain disadvantages attendant with the use of such attachment methods. For example, a disadvantage of the insert molding method may be low pull-out strength of the cord from the anchoring component. This is believed to be caused by the difficulty in general, conventional compression molding processes to form a secure attachment between the cord and anchoring components. When using an eyelet or small hole, the hole or the eyelet are related to the removal or absence of material from the anchoring component which may, in some cases, result in mechanical strength lost, or it may be difficult or not possible to place a hole or an eyelet in or on the anchoring component due to a low profile configuration or limited space.

Accordingly, there is a need in this art for novel medical devices for use in tissue fixation, wherein the devices have a flexible cord attached.

SUMMARY OF THE INVENTION

Therefore, a novel tissue repair device is disclosed. The tissue repair device of the present invention has a cannulated anchor member, and a cord made from a plurality of fibers. The cord has first and second ends. The anchor member has a longitudinal passage having first and second ends. The cord passes through the anchor passage and extends out from each end of the passage. The cord has a first end and a second end. A stopper is mounted to the end of the cord to prevent the cord from passing back through the anchor cannulation. Fibers that form the end of the cord to which the stopper is mounted are imbedded and spread apart within the stopper member. This enhances the attachment strength of the cord to the stopper. Optionally, the device has a second anchor member with a second stopper member mounted to the cord in the same manner.

Another aspect of the present invention relates to a method of molding the above described stopper around an end of the cord so that the fibers that form the cord are spread apart within the stopper.

Yet another aspect of the present invention is a novel method of repairing tissue using the novel tissue repair devices of the present invention.

The novel tissue repair devices having cords and cannulations overcome the disadvantages of the prior art by providing secure fixation and minimizing or eliminating the possibility of the cord separating from the anchor member.

These and other features and advantages of the present invention will become more apparent from the following description and accompanying drawings.

BRIEF DESCRIPTION OF THE DRAWINGS

FIG. 5b is an end view of the polymer tube of FIG. 5a.

DETAILED DESCRIPTION OF THE INVENTION

Figure 1:
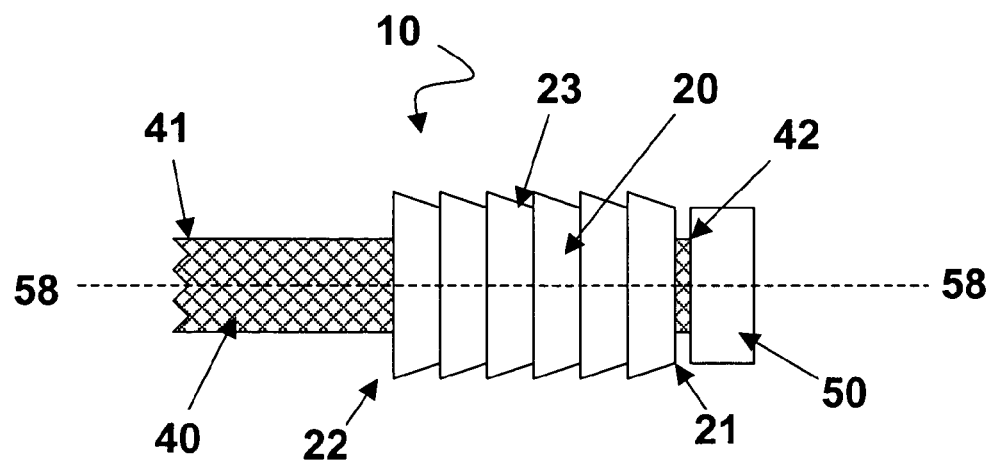
FIG. 1 is a side view of an embodiment of a tissue repair device of the present invention.
Figure 2:
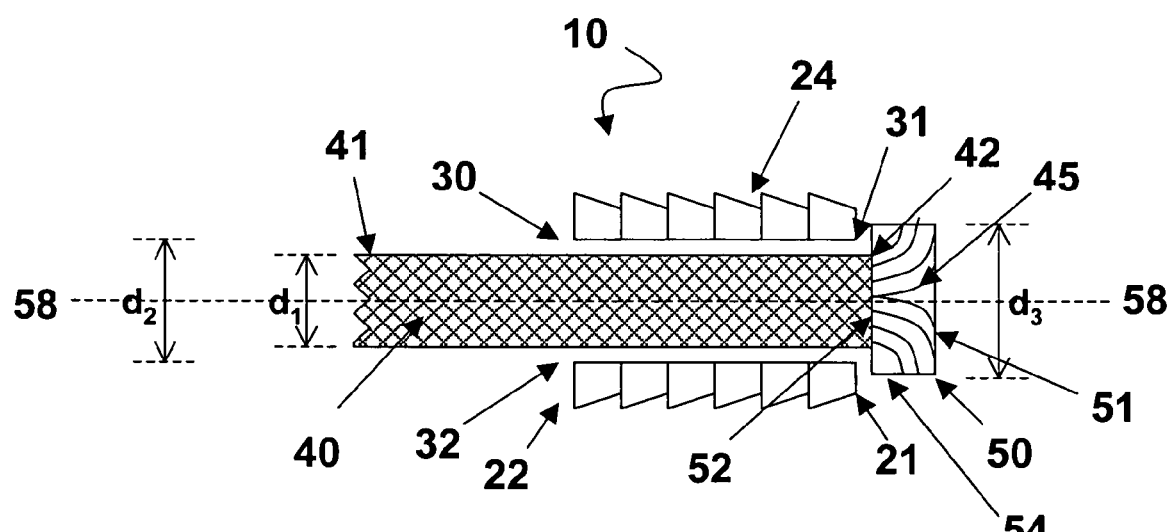
FIG. 2 is a cross-sectional view of the tissue repair device of FIG. 1.

The novel tissue repair devices of the present invention have a cannulated anchoring or anchor component through which a cord passes, and a stopper that prevents the cord from passing back through the anchor. The stopper is molded around an end of the cord so that the fibers that form the cord are spread apart within the stopper. This enhances the attachment strength of the cord to the stopper. In other words, the tensile force necessary to separate the cord from the stopper is increased surgical procedures, wherein there is a requirement to anchor at least a section of a cord (e.g., a tape or a surgical suture) within a bone bore An embodiment of the device 10 of the present invention is seen in FIGS. 1 and 2. Device 10 is seen to have a cannulated anchor member 20, a cord 40, and a stopper 50. Anchor member 20 has first end 21 and second end 22, and outer surface 23. A plurality of ridge members 24 are seen to extend out from anchor member 20 to assist in securing the anchor member 20 in tissue. If desired other types of conventional tissue securement members may be utilized including screw threads, spikes, projections having various geometric configurations such as pyramidal, cylindrical, hemispherical, etc. Anchor member 20 is also seen to have longitudinal passage 30 extending therethrough and to also have opening 31 in first end 21 and opening 32 in second end 22, both openings are in communication with passage 31. Longitudinal passage 30 may have a variety of cross-sections including circular, square, rectangular, oval and the like. Cord 40 is seen to be an elongated flexible member made from a plurality of fibers. Examples of cords that may be used in the devices 10 of the present invention include conventional sutures, tapes, ropes, and the like. Cord 40 is seen to have first end 41 and second end 42.

Referring to FIG. 2, fibers 45 are seen to be extending from second end 42 of cord 40 are embedded in stopper 50 such that fibers 45 are substantially spread apart within the stopper 40, and are generally angulated or curved (i.e., displaced) with respect to axis 58 of stopper 50. Stopper member or stopper 50 is seen to be a substantially disc-like member having top 51, bottom 52 and side 54. The stopper member 50 may have a variety of geometric configuration including spheres, cubes, cylinders, pyramids and combinations thereof and the like. As mentioned previously above, anchor member 20 is cannulated and has longitudinal passage 30. The maximum dimension of the cross-section of passage 30 has dimension $d_2$ that is sufficient for the through passage of cord 40 (with dimension $d_1$) through anchor member 20. Stopper member 50 has outer dimension $d_3$ sufficiently greater than $d_2$ to effectively prevent it from passing through longitudinal passage 30 of anchor member 20.

As previously mentioned above, cannulated anchor member 20 is shown in FIGS. 1 and 2 as having a series of teeth or ridges 24 for engagement of tissue, for example such as by an interference fit, when anchor member 20 is deployed in tissue such as bone. Anchor member 20 may also be of a threaded screw design for deployment in bone. It is also possible to mount conventional arc members or wing members to the anchor member 20 for the engagement of tissue.

Cord 40 is composed of fibers, and may be in any of the conventional forms known in textile technologies and useful in medical devices. These forms include braids, weaves, and knits. If braided, cord 40 can be in the form of a biaxial, triaxial, or tailored braid, or a braid formed by other known braiding methods.

Suitable materials from which cannnulated anchor member 20 and cord 40 may be formed include conventional biocompatible polymers such as aliphatic polyesters, polyorthoesters, polyanhydrides, polycarbonates, polyurethanes, polyamides and polyalkylene oxides and the like and equivalents. They also can be formed from conventional biocompatible metals, glasses or ceramics, or from autograft, allograft, or xenograft bone tissues.

Anchor member 20 and cord 40 further can be made from combinations of metals, ceramics, glasses and polymers.

The biocompatible materials can be biodegradable or non-biodegradable. Biodegradable materials, such as polymers, readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment isretained by the body.

In one embodiment, cannulated anchor member 20 or cord 40 comprise biodegradable aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, epsilon-caprolactone, p-dioxanone (1,4-dioxan-2-one), and trimethylene carbonate (1,3-dioxan-2-one).

Several preferred materials for anchoring member 20 or cord 40 are poly(lactic acid), or PLA, and a copolymer of lactic acid with glycolic acid, or poly(lactide-co-glycolide) (PLGA), in a mole ratio of 95 lactic acid to 5 glycolic acid.

In another embodiment, the materials from which anchor member 20 and cord 40 are made will be conventional biodegradable glasses or ceramics including mono-, di-, tri-, alpha-tri-, beta-tri-, and tetra-calcium phosphate, hydroxyapatite, calcium sulfates, calcium oxides, calcium carbonates, magnesium calcium phosphates, phospate glasses, bioglasses, and mixtures thereof, equivalents thereof and the like.

In another embodiment, the materials from which anchor member 20 is made are combinations of biodegradable ceramics and polymers. Composites are prepared by incorporating biodegradable ceramic reinforcements such as particles in a biodegradable polymer matrix.

Anchor member 20 may be made in a conventional manner using known methods including injection molding, machining, extrusion, and the like.

Stopper member 50 is dimensioned ($d_3$) so that it will not pass through passage 30 dimension $d_2$ of anchoring component 20. Suitable materials from which stopper member 50 may be formed include the biocompatible and biodegradable polymers mentioned above. As with anchor member 20, stopper 50 may be made from combinations of biodegradable ceramics and polymers, or a polymer reinforced with another polymer, such as a short-fiber polymer reinforcing a polymer matrix. The materials used to form stopper 50 must be flowable, so that they may infiltrate and surround fibers 45 of end 42 of cord 40. Preferred materials include thermoplastic biocompatible and biodegradable polymers.

One particularly preferred material for stopper 50 is a copolymer of epsilon-caprolactone with p-dioxanone, or poly (epsilon-caprolactone-co-p-dioxanone), in a mole ratio of 95 epsilon-caprolactone to 5 p-dioxanone.

As illustrated in FIG. 2, fibers 45 extending from end 42 of cord 40 are embedded in stopper 50 such that fibers 45 are sufficiently spread apart within stopper member 50 to effectively retain stopper member 50 onto end 42. The spreading of fibers 45 within stopper member 50 occurs simultaneously during the forming of stopper member 50.

In a preferred embodiment of the present invention, one end 42 of cord 40 is encapsulated in a thermoplastic polymer via a compression molding process as described herein. In this case, stopper 50 is formed of a thermoplastic polymer that has a lower melting point than the materials from which the cord 40 is made.

Figure 3:
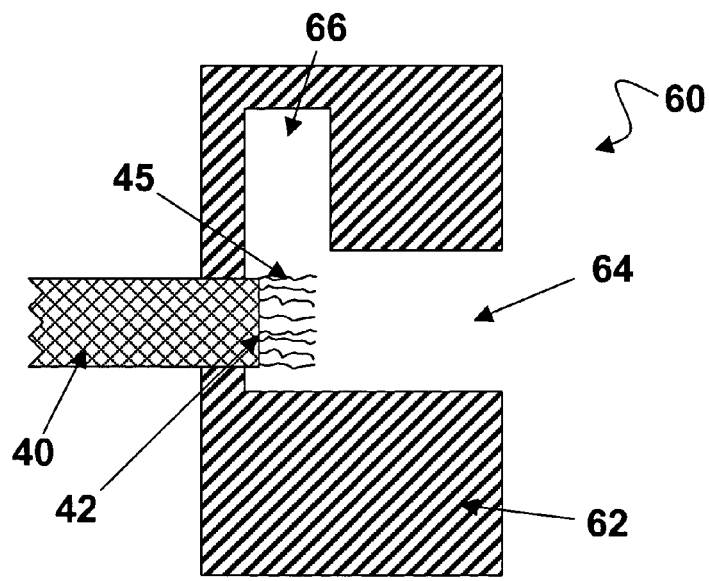
FIG. 3 is a detailed cross-sectional view of a schematic of a molding assembly for forming a stopper assembly for the tissue repair device of the present invention.
Figure 4A:
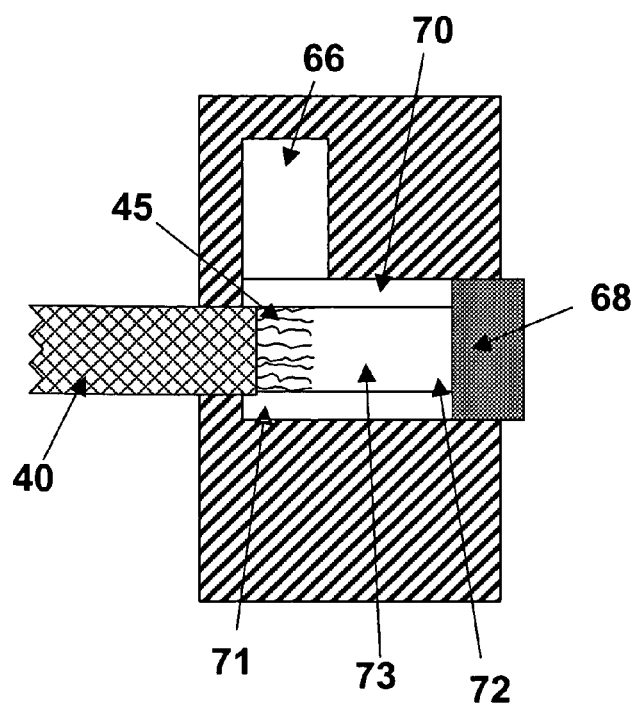
FIG. 4a illustrates the molding assembly of FIG. 3 at the onset of the molding process showing the fibers at the end of the cord prior to being molded into the stopper.
Figure 4B:
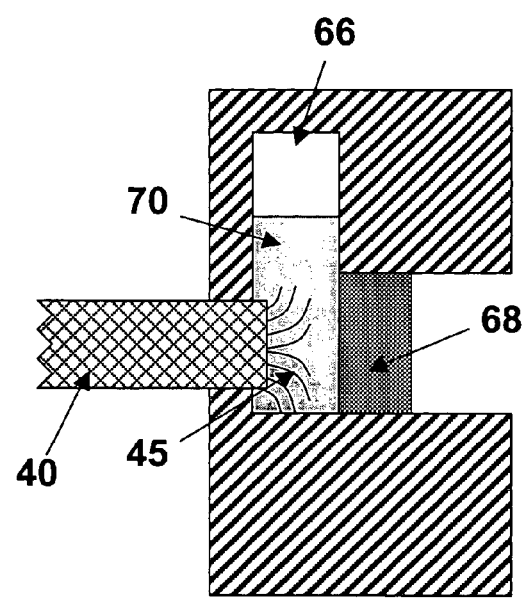
FIG. 4b illustrates the molding assembly of FIG. 3 at the conclusion of the molding process showing the fibers of the cord end spread apart in the molded stopper.

One method of fabricating assembled device 10 of the present invention is illustrated schematically in FIGS. 3, 4a and 4b. In this embodiment of the method, compression molding die assembly 60 is utilized. Die assembly 60 includes a mold portion 62 having a main cavity 64 and a side cavity 66.

In the first step of the fabrication process, second end 42 of cord 40 is disposed in main cavity 64 of die assembly 60 such that fibers 45 are substantially spread apart in cavity 64. At this point, the fibers 45 at the end 43 of cord 40 are substantially separated from their textile architecture via a fraying, teasing or unraveling procedure. The purpose of this procedure is to maximize the available surface area of fibers 45 to the flow front in die assembly 60.

Next, as shown in FIG. 4a, a prefabricated polymer tube 70, having passage 43 and opposed first and second open ends 71 and 72, consisting of the polymer that will be used to form stopper 50, is disposed in main cavity 64 of die assembly 60 so that it surrounds fibers 45 at the second end 42 of cord 40, wherein end 42 is at least partially disposed through first open end 71 into passage 73. Conventional extrusion or injection molding may be used to form prefabricated polymer tube 70. Plunger 68 is then disposed in main cavity 64 of die assembly 60 as shown.

The entire assembly is then heated to a temperature sufficient to melt prefabricated polymer tube 70 such that the polymer material is effectively flowable within cavity 64 under pressure in response to the movement of plunger 68. As mentioned previously, polymer tube 70 must be formed of a thermoplastic polymer that has a lower melting point than the materials that comprise fibers 45 of cord 40.

In the next step, plunger 68 is moved in the direction of end 42 and fibers 45. The movement of plunger 68 axially in main cavity 64 forces the fibers 45 to spread apart about end 42, as shown in FIG. 4b. This results in fibers 45 being spread apart within melted polymer that was tube 70. The molten polymer compressed out of main cavity 64 flows into side cavity 66.

The cord and stopper member assembly is cooled, and melted polymer solidifies. After removal from mold 60, the solidified polymer/cord 40 combination is trimmed to yield the cord 40/stopper 50 assembly of the present invention.

Figure 5A:
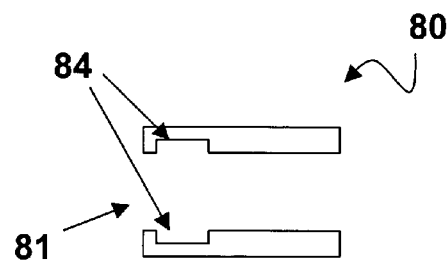
FIG. 5a is a cross-sectional view of an alternative configuration of a polymer tube useful in forming the stopper assembly of the present invention.
Figure 5B:
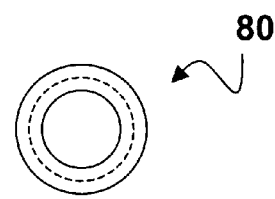

In FIG. 4a, prefabricated polymer tube 70 is shown as a tube with uniform wall thickness. In an alternative embodiment, tube 70 can have a cavity within the tube wall. A tube 80 with an annular wall cavity 84 disposed within end 81 of tube 80 is shown in FIGS. 5a and 5b in cross-section and end view, respectively. This embodiment of tube 80 is disposed in mold assembly 60 such that wall cavity 84 is located adjacent to end 42 of cord 40 and fibers 45. When plunger 68 is moved axially in the direction of fibers 45, fibers 45 will be displaced into wall cavity 84, yielding fibers 45 spread apart when polymer flows in mold cavity 64.

The attachment strength of cord 40 to stopper member 50 in the cord 40/stopper 50 assembly produced according to the present invention is largely enhanced by the process of the present invention in which the ends 45 are spread out and surrounded by polymer in stopper 50.

Figure 6:
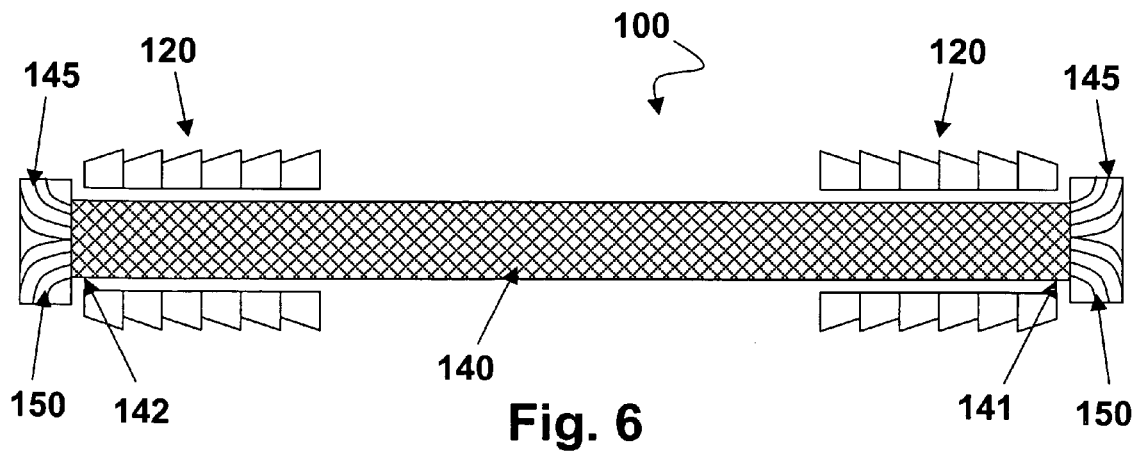
FIG. 6 is a cross-sectional view of a device that has a second anchor member with a first and a second stopper member mounted to the cord in the same manner as the tissue repair device of FIG. 1.

In another embodiment of the tissue repair devices of the present invention, shown in FIG. 6, device 100 has anchor members 120 mounted to each end of the cord 140 in a similar manner with the fibers 145 of ends 141 and 142 separated and spread in the anchor members 150.

The tissue repair devices of the present invention can be used to repair a variety of tissues in various surgical procedures. The devices can be used to approximate tissue, e.g., vertebral repair, approximation of soft tissue to the surface of a bone, etc. Those skilled in this art will appreciate that the anchors of the present invention may also be used with other types of procedures and tissues. The devices may be used in various tissue repair procedures including rotator cuff repair, spinal repair procedures, etc.

The following example is illustrative of the principles and practice of this invention, although not limited thereto.

EXAMPLE 1

Forming Cord/Stopper Assemblies

In this example, a general compression molding process was used to form an assembly of a cord 30 with a stopper mounted to one end of the cord.

The material used to form the stopper was 95/5 poly(epsilon-caprolactone-co-p-dioxanone) with an Inherent Viscosity (IV) of 1.5dl/gm (measured in chloroform at 25° C.). The 95/5 poly(epsilon-caprolactone-co-p-dioxanone) was prefabricated into a short tube with dimensions of: OD 0.38 centimeters, ID 0.23 centimeters, and 0.30 centimeters long (by extrusion under an extrusion temperature of 85° C.).

The cord was a three dimensional woven cord made using 95/5 poly(lactide-co-glycolide)(95/5 PLGA) fibers. The fibers are sold under the tradename PANACRYL, (Ethicon, Inc., Somerville, N.J.). The cord was 3D woven with 100 Denier fiber and a diameter of 2 millimeter at Fiber Concepts, Inc. (Conshohocken, Pa.).

An anchor member was made using 95/5 poly(lactide-co-glycolide) by injection molding billets of the material, and machining them into anchors.

The end of the cord was teased and trimmed before it was placed into the mold cavity. A prefabricated short tube was placed into the mold so that the loose fibers at the end of the cord were inside the tube. The plunger was then put in place, and the mold was closed and placed into a compression molder (Model 2696, Carver, Inc., Wabash, Ind.). The mold was heated to a temperature of 65° C. for 3 minutes. The plunger was then moved in the direction of the fibers and the mold was cooled to a temperature of 25° C. for 3 minutes under compression pressure.

As a control, the same procedure was used with the exception that the plunger was not moved in the direction of the fibers after the mold was heated to a temperature of 65° C. for 3 minutes. So, in the control the fibers were not spread by the movement of the plunger.

The pullout strength of the two assemblies was tested. Pullout tests were performed using an Instron 4501 test frame. The cord was first loaded on a polyurethane foam block with a pre-drilled hole with diameter of 2.68 mm, which was fixed in place by a special clamp that allows movement in the X-Y plane but not the Z (pulling) direction. The cord end was held tightly by the grips and then a tensile testing procedure was performed with a cross-head rate of 0.1 millimeter/second. The pullout strength of the control was 18 pounds-force (lbf), while that of the assembly with spread fibers was 35 pounds-force (lbf).

EXAMPLE 2

Surgical Procedure

A patient is prepared for spinal fusion surgery in a conventional manner. The surgery will fuse one or more levels of the spinal column. The patient is anesthetized in a conventional manner. The tissue repair site is accessed by making an incision through the abdominal cavity and dissecting down to the spinal column. A sterile device of the present invention is prepared for implantation into the patient, the device having anchor members mounted to each end of the cord. The operative site is prepared to receive the anchor members of the repair device by dissecting through the ligamentous structure attached to the vertebral bodies of the spinal column that will be fused. A discectomy procedure is performed to remove the disc of the vertebral level to be fused and a bone graft is inserted into the discs space. A hole is drilled into the vertebral body above and below the disc space. The anchor bodies are then inserted into drilled holes in the adjoining vertebrae to be fused. The cord of the device is used to prevent migration of the bone graft in order to complete the tissue repair. The incision is approximated in a conventional manner using conventional surgical sutures. The incision is bandaged in a conventional manner, thereby completing the surgical procedure.

The novel devices and method of the present invention provide the patient and surgeon with multiple advantages. The advantages include increased pull-out strength and a decoupling of the anchor member from the cord.

Although this invention has been shown and described with respect to detailed embodiments thereof, it will be understood by those skilled in the art that various changes in form and detail thereof may be made without departing from the spirit and scope of the claimed invention.

We claim:

1. A method of molding a polymeric medical device comprising the steps of:
- providing a polymer cord having a first end and a second end, said cord comprising a plurality of flexible fibers having a textile architecture;
- substantially separating fibers at the one end of the cord from their textile architecture, wherein the separated fibers are both flexible and moveable;
- disposing one end of the cord in a die cavity;
- providing a thermoplastic polymer tube having an inner passage;
- disposing the polymer tube in the die cavity so that it substantially surrounds the fibers such that the fibers are at least in part within the inner passage;
- disposing a plunger in the die cavity adjacent to the tube;
- heating the die cavity to a temperature sufficient to effectively melt the prefabricated polymer tube;
- moving the plunger axially in the die cavity in the direction of the fibers to force the fibers to spread apart while forming a stopper member from the melted thermoplastic polymer tube such that the fibers are in a spread apart configuration within the stopper; and,
- cooling the die cavity,
- wherein the cord and the stopper member comprise biodegradable aliphatic polymers, copolymers, or blends formed from monomers selected from the group consisting of lactic acid, lactide, glycolic acid, glycolide, epsilon-caprolactone, 1, 4-dioxan-2-one, and (1,3-dioxan-2-one).

2. The method of claim 1, wherein the prefabricated polymer tube has an interior wall cavity in communication with the inner passage.

3. The method of claim 1, wherein the cord is in a form selected from the group consisting of braid, weave, or knit.

4. The method of claim 1, wherein the cord comprises a braid and is in a form selected from the group consisting of bixial braid and triaxal braid.

5. The method of claim 1, wherein the cord comprises poly(lactic acid).

6. The method of claim 1, wherein the cord comprises poly(lactide-co-glycolide) in a mole ratio of 95 lactic acid to 5 glycolic acid.

7. The method of claim 1, wherein the stopper member comprises poly(epsilon-caprolactone-co-1 ,4-dioxan-2-one), in a mole ratio of 95 epsilon-caprolactone to 5 1 ,4-dioxan-2-one.

* * * * *